United States Patent [19]

Schwab et al.

[11] Patent Number: 4,667,028

[45] Date of Patent: May 19, 1987

[54] PROCESS FOR THE PREPARATION OF CEPHEM COMPOUNDS

[75] Inventors: Wilfried Schwab, Kelkheim; Walter Dürckheimer, Hattersheim am Main; Reiner Kirrstetter, Kelkheim; Rudolf Lattrell, Königstein, all of Fed. Rep. of Germany

[73] Assignee: Hoechst Aktiengesellschaft, Frankfurt, Fed. Rep. of Germany

[21] Appl. No.: 607,403

[22] Filed: May 4, 1984

[30] Foreign Application Priority Data

May 7, 1983 [DE] Fed. Rep. of Germany ....... 3316798

[51] Int. Cl.$^4$ ............................................ C07D 501/46
[52] U.S. Cl. ...................................... 540/222; 540/225
[58] Field of Search ................... 544/22, 25; 540/222, 540/225

[56] References Cited

U.S. PATENT DOCUMENTS 4,258,041  3/1981  O'Callaghan ......................... 544/22
4,266,049  5/1981  Bonjouklian ......................... 544/16
4,396,620  8/1983  Lunn ..................................... 544/22

FOREIGN PATENT DOCUMENTS 0060144  9/1982  European Pat. Off. .
0070706  1/1983  European Pat. Off. .

Primary Examiner—Esther M. Kepplinger
Assistant Examiner—Robert Benson
Attorney, Agent, or Firm—Finnegan, Henderson, Farabow, Garrett & Dunner

[57] ABSTRACT

Process for the preparation of cephem compounds of the formula

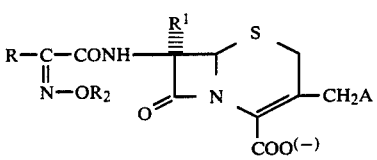

2 Claims, No Drawings

PROCESS FOR THE PREPARATION OF CEPHEM COMPOUNDS

The invention relates to a process for the preparation of cephem compounds of the general formula I

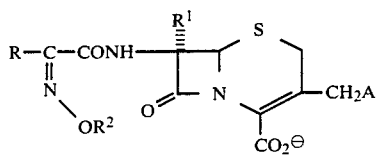

(I)

in which R denotes a thiazolyl radical

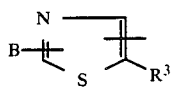

or a 1,2,4-thiadiazolyl radical

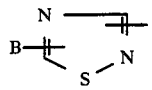

in which
$R^3$ represents hydrogen or halogen and B represents an optionally substituted amino group, and wherein $R^1$ denotes hydrogen or methoxy,
$R^2$ denotes hydrogen, optionally substituted $C_1$–$C_6$-alkyl, optionally substituted $C_2$–$C_6$-alkenyl, $C_2$–$C_6$-alkinyl, $C_3$–$C_7$-cycloalkyl, $C_3$–$C_7$-cycloalkyl-$C_1$–$C_6$-alkyl, $C_4$–$C_7$-cycloakenyl or the group $$(CH_2)_n(\overset{R^4}{\underset{R^5}{C}})_m R^6,$$

in which m and n are each 0 or 1,
$R^4$ and $R^5$ can be identical or different and denote hydrogen, aryl or a $C_1$–$C_4$-alkyl group, or, together with the carbon to which they are bonded, form a methylene or $C_3$–$C_7$-cycloalkylidene group, it being possible for the $C_1$–$C_4$-alkyl and the $C_3$–$C_7$-cycloalkylidene group also to be further monosubstituted or polysubstituted, and
$R^6$ denotes a COOH, CN or $CONH_2$ group, it being possible for the latter to be monosubstituted or disubstituted on the nitrogen, and
A denotes a quinolinium

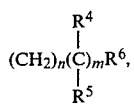

or an isoquinolinium

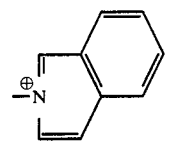

radical, each of which can also be monosubstituted or polysubstituted by identical or different substituents from the group comprising optionally substituted $C_1$–$C_6$-alkyl, $C_1$–$C_6$-alkoxy, halogen, trifluoromethyl and hydroxyl, or denotes a phenanthridinium radical, or denotes a pyridinium radical

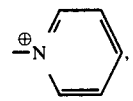

which can be monosubstituted or polysubstituted by identical or different substituents from the group comprising optionally substituted $C_1$–$C_6$-alkyl, it being possible for 2 alkyl groups in the ortho-position also to be linked to form an optionally substituted di- to deca-methylene ring in which one ring carbon atom can be replaced by a heteroatom and which can furthermore also contain one or two double bonds; optionally substituted $C_2$–$C_6$-alkenyl, $C_2$–$C_6$-alkinyl, $C_3$–$C_7$-cycloalkyl and $C_3$–$C_7$-cycloalkylmethyl, it being possible for the ring in these last two substituents also to be substituted; $C_4$–$C_7$-cycloalkenyl, optionally substituted $C_1$–$C_6$-alkoxy, $C_2$–$C_6$-alkenyloxy and $C_2$–$C_6$-alkinyloxy, halogen, trifluoromethyl and hydroxyl, optionally substituted phenyl, benzyl and heteroaryl, formyl and ketalized formyl, optionally substituted $C_1$–$C_6$-alkylcarbonyl, which can also be in ketalized form, arylcarbonyl and carbamoyl, and in which the $R^2O$ group is in the syn-position.

The present invention particularly relates to compounds in which R and $R^1$ have the above meanings, B denotes an amino group, which can be substituted by amino-protected groups, $R^2$ denotes hydrogen, $C_1$–$C_6$-alkyl, which can be monosubstituted or polysubstituted by halogen, $C_1$–$C_6$-alkylthio, $C_1$–$C_6$-alkoxy, aryl or heteroaryl, or denotes $C_2$–$C_6$-alkenyl, which can be monosubstituted or polysubstituted by halogen; or denotes $C_2$–$C_3$-alkinyl, $C_3$–$C_6$-cycloalkyl, $C_3$–$C_6$-cycloalkyl-$C_1$–$C_6$-alkyl, $C_4$–$C_7$-cycloalkenyl, and in which the group $$(CH_2)_n(\overset{R^4}{\underset{R^5}{C}})_m R^6$$

has the above meaning, and
A denotes a quinolinium or isoquinolinium radical, each of which can also be monosubstituted or polysubstituted by identical or different substituents from the group comprising $C_1$–$C_6$-alkyl, which can be substituted by hydroxyl; $C_1$–$C_6$-alkoxy,
halogen,
trifluoromethyl and
hydroxyl,
or denotes a pyridinium radical

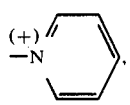

which can be monosubstituted or polysubstituted by identical or different substituents from the group comprising $C_1$–$C_6$-alkyl, which can be monosubstituted or polysubstituted by hydroxyl; formyl and $C_1$–$C_6$-alkylcarbonyl, the carbonyl groups of which can also be in ketalized form, sulfo, carbamoyl, $C_1$–$C_6$-alkoxy and hydroxy-$C_1$–$C_6$-alkoxy, it also being possible for 2 alkyl groups to be linked to form an optionally substituted di- to deca-methylene ring in which one ring carbon atom can be replaced by a heteroatom and which can furthermore also contain one or two double bonds, $C_2$–$C_6$-alkenyl, which can be substituted by hydroxyl, $C_2$–$C_6$-alkinyl, $C_3$–$C_7$-cycloalkyl and $C_3$–$C_7$-cycloalkylmethyl, it being possible for the ring in these two substituents also to be substituted by hydroxyl or halogen, $C_4$–$C_7$-cycloalkenyl, $C_1$–$C_6$-alkoxy, which can be substituted by hydroxyl, $C_2$–$C_6$-alkenyloxy and $C_2$–$C_6$-alkinyloxy, halogen, trifluoromethyl and hydroxyl, phenyl, benzyl and heteroaryl, which can also be substituted by halogen, formyl and ketalized formyl, $C_1$–$C_6$-alkylcarbonyl, which can also be substituted by hydroxyl and can also be in ketalized form, arylcarbonyl and carbamoyl, and in which, in these preferred compounds falling within the general formula I, the $R^2O$ group is also in the syn-position.

Possible optional substituents of the di- to decamethylene ring mentioned under A, in which one ring carbon atom can be replaced by a heteroatom and which can furthermore also contain one or two double bonds, are, in particular, the following substituents, which may occur individually or in combination, but preferably individually: $C_1$–$C_6$-alkyl, $C_1$–$C_4$-alkoxy, hydroxymethyl, halogen, hydroxyl, oxo and exomethylene.

These substituents may occur on the above rings fused onto the pyridinium radical, independently of whether the particular ring is saturated, unsaturated or interrupted by a heteroatom.

The ring fused onto the pyridinium radical can contain 2 to 10 ring members (di- to deca-methylene), but preferably 3 to 5 ring members, and thus can be, for example, a cyclopenteno, cyclohexeno or cyclohepteno or cyclohepteno ring. If such a fused-on ring contains a double bond, examples which may be mentioned are the dehydrocyclopentadieno, dehydrocyclohexadieno and dehydrocycloheptadieno ring. If a carbon atom in such rings is replaced by a heteroatom, possible heteroatoms are, in particular, oxygen and sulfur. Examples which may be mentioned of fused-on rings which contain an oxygen atom and one or two double bonds are furo, pyrano, dihydrofuro and dihydropyrano; possible fused-on rings which contain a sulfur atom and one or two double bonds are thieno, thiopyrano, dihydrothieno and dihydrothiopyrano. Of the fused-on rings containing a heteroatom, those rings which contain only one double bond are particularly suitable for substitution, in particular by the abovementioned substituents.

Examples of particularly preferred substituents are the following:

B: $NH_2$, $HCONH$, $CF_3CONH$, $CCl_3CONH$, $C_6H_5CH_2CONH$, $(C_6H_5)_3CNH$, $HSO_3NH$ and $(CH_3)_2CH=N$, R:

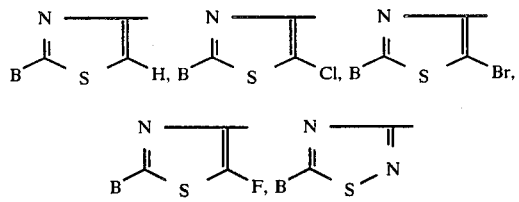

$R^1$: hydrogen and $OCH_3$ $R^2$: hydrogen, $C_1$–$C_6$-alkyl, such as, for example, methyl, ethyl, propyl, isopropyl and butyl, preferably methyl and ethyl; $C_1$–$C_2$-halogenoalkyl, for example alkyl which is substituted by chlorine, bromine, iodine or fluorine, preferably trifluoroethyl, difluoromethyl and 2,2,3,3-tetrafluoropropyl, alkyl which is substituted by aryl, such as, for example, phenyl, tolyl and chlorophenyl, in particular benzyl, alkyl which is substituted by heteroaryl, such as, for example, 1,3-thiazol-4-yl-substituted alkyl, in particular 1,3-thiazol-4-yl-methyl, $C_2$–$C_6$-alkenyl, such as, for example, vinyl, allyl, isopropenyl and methallyl, in particular allyl and methallyl, $C_2$–$C_6$-alkenyl which is substituted by halogen, such as, for example, chlorine or bromine, in particular 3-chloropropen-2-yl, 2-bromopropen-2-yl and 2-chloropropen-2-yl;

$C_2$–$C_3$-alkinyl, such as, in particular, propargyl, $C_3$–$C_7$-cycloalkyl, such as, in particular, cyclopropyl, cyclobutyl and cyclopentyl, $C_3$–$C_7$-cycloalkyl-$C_1$–$C_6$-alkyl, such as, in particular, cyclopropylmethyl and cyclobutylmethyl, $C_4$–$C_7$-cycloalkenyl, such as, in particular, cyclopenten-1-yl, and the group

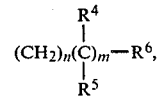

in which $R^4$ and $R^5$ can be identical or different and can denote hydrogen, aryl, preferably phenyl, or $C_1$–$C_4$-alkyl, such as, for example, methyl, ethyl, propyl, isopropyl, butyl or sec.-butyl, preferably methyl or ethyl, and in particular methyl, or in which $R^4$ and $R^5$, together with the carbon atom to which they are bonded, can form a methylene group or a $C_3$–$C_7$-cycloalkylidene group, such as, for example, cyclopropyl, cyclobutyl, cyclopentyl, cyclohexyl or cycloheptyl, preferably cyclopropyl, cyclobutyl, cyclopentyl or cyclohexyl, it being possible for the cycloalkylidene group to be substituted, for example by $C_1$–$C_4$-alkyl, preferably methyl, by halogen, preferably fluorine and chlorine, or by alkylene with 3–6 carbon atoms, m=0 or 1 and n=0 or 1, the sum of m and n being 1 or 2.

Preferred examples of the group

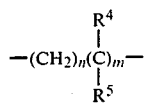

are the following:

If n=0 and m=1:

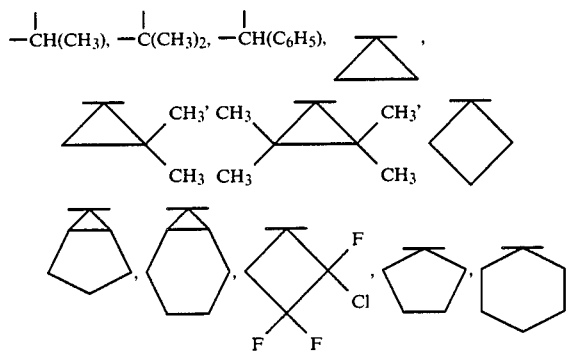

and
if m=0 and n=1: —CH$_2$—, and
if n and m=1: —CH$_2$—C(=CH$_2$)—.

$R^6$: the COOH, CN and CONH$_2$ groups, and carbamoyl which is substituted by C$_1$–C$_6$-alkyl, preferably methy or ethyl.

A: a quinolinium or an isoquinolinium radical, each of which can also be monosubstituted or polysubstituted by identical or different substituents from the group comprising C$_1$–C$_6$-alkyl, such as, for example, methyl, ethyl, propyl and isopropyl, preferably methyl, methoxy, hydroxyl, halogen and trifluoromethyl, or a pyridinium radical, which can be monosubstituted or polysubstituted, preferably mono-, di- or tri-substituted, in particular mono- or di-substituted, for example by C$_1$–C$_4$-alkyl, such as, in particular, methyl, ethyl, propyl, isopropyl, n-butyl, sec.-butyl, tert.-butyl, dimethyl, trimethyl, methyl and ethyl, methyl and propyl, methyl and isopropyl or ethyl and ethyl;

hydroxy-C$_1$–C$_4$-alkyl, such as, in particular, hydroxymethyl, hydroxyethyl, hydroxypropyl, hydroxyisopropyl, hydroxybutyl, hydroxy-sec.-butyl or hydroxy-tert.-butyl, it also being possible, for example, for the alkyl radical to carry two or three hydroxyl groups; formyl-C$_1$–C$_4$-alkyl, such as, in particular, formylmethyl, C$_1$–C$_4$-alkylcarbonyl-C$_1$–C$_4$-alkyl, such as, in particular, methylcarbonylmethyl, ethylcarbonylmethyl, methylcarbonylethyl and ethylcarbonylethyl; C$_3$–C$_4$-alkenyl, such as, in particular, allyl, 2-methallyl and buten-3-yl, which can also be substituted by hydroxyl, such as, in particular, hydroxyallyl and hydroxybutenyl; C$_3$-alkinyl, such as, in particular, propargyl; C$_3$–C$_6$-cycloalkyl and C$_3$–C$_6$-cycloalkyl-methyl, the carbon number relating to the cycloalkyl part, such as, in particular, cyclopropyl, cyclobutyl, cyclopentyl, cyclohexyl and cyclopentylmethyl, it also being possible for the rings to be substituted, for example by hydroxyl, such as, in particular, 1-hydroxy-1-cyclopentyl and 1-hydroxy-1-cyclohexyl, or by halogen, preferably chlorine;

C$_5$–C$_6$-alkenyl, such as, in particular, cyclopenten-1-yl and cyclohexen-1-yl;

C$_1$–C$_6$-alkoxy, such as, in particular, methoxy and ethoxy, halogen, such as, in particular, 3-fluoro, 3-chloro, 3-bromo or 3-iodo; hydroxyl, in particular 3-hydroxy; trifluoromethyl, in particular 3-trifluoromethyl; phenyl and benzyl, which can also be substituted, for example by halogen, in particular chlorine, such as, for example, 4-chlorobenzyl; 2'-thienyl and 3'-thienyl; C$_1$–C$_4$-alkylcarbonyl, in particular acetyl and propionyl, preferably acetyl; and formyl, benzoyl and carbamoyl.

If A is a pyridinium radical which is substituted by two alkyl groups linked to form a di- to deca-methylene ring, which in turn can be monosubstituted or polysubstituted, preferably monosubstituted, and can contain one or two double bonds, the following fused-on ring systems are very particularly suitable here:

Cyclobuteno, cyclopenteno, hydroxycyclopenteno, oxocyclopenteno, hydroxymethylcyclopenteno, exomethylencyclopenteno, carboxycyclopenteno and carbamoyl-cyclopenteno, cyclohexeno, hydroxycyclohexeno, oxocyclohexeno, hydroxymethylcyclohexeno, exomethylenecylcohexeno, carboxycyclohexeno and carbamoylcyclohexeno, cyclohepteno, hydroxy-, oxo-, hydroxymethyl-, exomethylene- and carboxy-cyclohepteno and carbamoyl-cyclohepteno; and dehydro-cyclopenteno, dehydrocyclohexeno and dehydro-cyclohepteno.

If a ring carbon atom in the abovementioned fused-on ring systems is replaced by a heteroatom, in particular oxygen, particularly suitable ring systems are:

Furo[2,3-b]pyridine, furo[3,2-b]pyridine, furo[2,3-c]pyridine, furo[3,2-c]pyridine, thieno[2,3-b]pyridine, thieno[3,2-b]pyridine, thieno[2,3-c]pyridine, thieno[3,2-c]pyridine, thieno[3,4-b]pyridine and thieno[3,4-c]pyridine.

The process according to the invention for the preparation of compounds of the formula I comprises reacting a compound of the general formula II

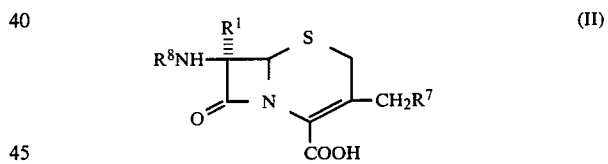

in which $R^1$ has the meaning given for formula I, $R^7$ denotes a group which can be replaced by the base which corresponds to the radicals A of formula I and $R^8$ represents hydrogen or an emino-protective group, with the base on which the radical A defined in formula I is based and in the presence of tri-C$_1$–C$_4$-alkyl-iodosilane, preferably trimethyl- or triethyl-iodosilane, to form the compound of the general formula III

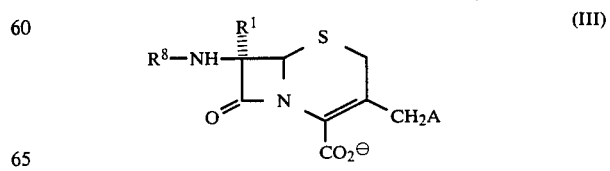

in which $R^1$, $R^8$ and A have the abovementioned meaning, and (a) splitting off any amino-protective group which may be present and (b) reacting the compound III, in which $R^8$ denotes hydrogen, either as such or in the form of a reactive derivative, with a 2-syn-oxyiminoacetic acid of the general formula IV

in which R and $R^2$ have the meaning given, or with a derivative of this compound which is activated at the carbonyl group.

The use of trimethyl-iodosilane is particularly preferred.

The starting compounds are known from the literature or can be prepared by processes which are known from the literature (cf., for example, German Offenlegungsschrift No. 2,716,707, German Offenlegungsschrift No. 3,118,732 and German Patent Applications Nos. P 32 07 840, P 32 47 613 and P 32 47 614).

Possible radicals $R^7$ are, in particular, acyloxy radicals of lower aliphatic carboxylic acids, preferably with 1 to 4 carbon atoms, such as, for example, acetoxy or propionyloxy, in particular acetoxy, which can optionally be substituted, such as, for example, chloroacetoxy or acetylacetoxy. Other groups are also possible for $R^7$, such as, for example, carbamoyloxy.

It is known from European Patent No. 64,740 and No. P 32 07 840.4 that compounds of the general formula I in which R denotes a 2-aminothiazol-4-yl radical and their physiologically acceptable acid addition salts have an excellent antibacterial activity. These compounds can be prepared, for example, from compounds of the general formula II via the compounds of the general formula III, which are obtained from II by direct reaction with the corresponding bases, preferably in water or aqueous mixtures as the solvent, and subsequent acylation with the acids of the formula IV.

It has now been found that the compounds of the general formula I are obtained in a surprisingly high yield by the process according to the invention if the nucleophilic replacement reaction on compounds of the general formula II is effected by a procedure in which the reaction is carried out from the beginning in the presence of an excess of the corresponding bases on which the radical A in formula I is based and of a tri-$C_1$-$C_4$-alkyl-iodosilane, preferably trimethyl-iodosilane, and the compounds of the general formula III formed are then acylated with compounds of the general formula IV.

The process according to the invention is carried out by adding the base corresponding to the radical A to a solution or suspension of the compound II in a suitable solvent, and then adding trimethyliodosilane. Instead of trimethyliodosilane, it is also possible to use, for example, a reaction mixture of iodine and hexamethyldisilane, which have first been reacted at temperatures between about 60° and 120° in a manner which is known from the literature, trimethyliodosilane being formed. The same good result can also be obtained by using triethyliodosilane, which is prepared in a manner which is known from the literature, instead of trimethyliodosilane.

The reaction is carried out at temperatures between about −5° and +100° C., preferably between +10° and 80° C.

Examples of suitable inert aprotic solvents are chlorinated hydrocarbons, such as methylene chloride, chloroform, dichloroethane, trichloroethane and carbon tetrachloride, lower alkyl-nitriles, such as acetonitrile or propionitrile, or frigands; in particular, methylene chloride is an outstanding solvent.

The base corresponding to the radical A is added in at least the stoichiometric amount up to a twenty-fold excess, and amounts which bond the quantity of hydrogen iodide liberated and leave at least 1 mole, preferably 2-5 moles, of the base available for substitution are preferably used.

Since, besides the group R7 to be replaced, other functional groups, such as, for example, the carboxyl group, in the starting compound II also react with trimethyliodosilane, the latter is added in at least a two-fold to about a five- to ten-fold excess, preferably in a three- to ten-fold excess.

Such functional groups can also be pre-silylated by addition of a silylating agent, such as, for example, bis-trimethylsilylacetamide, bistrimethylsilyltrifluoroacetamide, trimethylchlorosilane, hexamethyldisilazane or bistrimethylsilylurea, either in the absence or in the presence of a base, preferably the desired base on which the group A is based, in the amount described above. Trimethyliodosilane is then added in at least the stoichiometric amount or in excess, preferably in a two-fold up to a ten-fold excess.

If the base on which the radical A in formula I is based contains functional groups, such as, for example, hydroxyl groups and the like, these are preferably presilylated with one of the abovementioned silylating agents and then used in the reaction.

The reaction products of the formula III can be isolated from the aqueous phase, obtained by addition of water or aqueous mineral acids, for example dilute HCl, HBr, HI or $H_2SO_4$, in the customary manner, for example by freeze-drying the aqueous phase, chromatography, precipitation by addition of organic solvents or precipitation from the aqueous solution in the form of a sparingly soluble salt, for example a hydriodide salt.

The compound of the general formula III is then acylated with carboxylic acids of the general formula IV, any amino-protective group $R^8$, for example a tert.-butyl, benzyl, trityl, benzhydryl, formyl, trichloroacetyl, trifluoroacetyl, sulfo or dimethylaminomethylene group, which may be present to facilitate the replacement reaction being first split off in a manner which is known per se.

If the carboxylic acids of the general formula IV themselves are used as acylating agents, the reaction is advantageously carried out in the presence of a condensing agent, for example a carbodiimide, such as, for example, N,N'-dicyclohexylcarbodiimide.

The carboxylic acids of the general formula IV can be activated in a particularly advantageous manner by treatment with certain carboxylic acid amides and, for example, phosgene, phosphorus pentachloride, tosyl chloride, thionyl chloride or oxalyl chloride, as described in German Patent No. 2,804,040.

Particularly suitable activated derivatives of the carboxylic acids of the general formula IV are also halides, preferably chlorides, which are obtained in a manner which is known per se by treatment with halogenating agents, such as, for example, phosphorus pentachloride, phosgene or thionyl chloride, under the mild reaction conditions known from the literature for cephalosporin chemistry.

Other suitable activated derivatives of the carboxylic acids of the general formula IV are the anhydrides and mixed anhydrides, azides and activated esters and thioesters, preferably with p-nitrophenol, 2,4-dinitrothioesters, phenol, methylenecyanohydrin, N-hydroxysuccinimide and N-hydroxyphthalimide, in particular those with 1-hydroxybenzotriazole, 6-chloro-1-hydroxybenzotriazole and 2-mercaptobenzothiazole. Particularly suitable mixed anhydrides are those with lower alkanoic acids, such as, for example, acetic acid, and particular preferably those with substituted acetic acids, such as, for example, trichloroacetic acid, pivalic acid or cyanoacetic acid. The mixed anhydrides with carbonic acid half-esters, which are obtained, for example, by reacting the carboxylic acids of the formula IV, in which the amino group is protected, with benzyl, p-nitrobenzyl, iso-butyl, ethyl or allyl chloroformate, are also particularly suitable. The activated derivatives can be reacted as isolated substances or as substances produced in situ.

In general, the cephem derivatives of the general formula III are reacted with a carboxylic acid of the general formula IV or an activated derivative thereof in the presence of an inert solvent. Particularly suitable solvents are chlorinated hydrocarbons, such as, preferably, methylene chloride and chloroform; ethers, such as, for example, diethyl ether, tetrahydrofuran and dioxane; ketones, such as, preferably, acetone and butanone; amides, such as, preferably, dimethylformamide and dimethylacetamide, or pyridine. It may also prove to be advantageous to use mixtures of the solvents mentioned. This is frequently the case if the cephem compound of the general formula III is reacted with an ativated derivative produced in situ, of a carboxylic acid of the formula IV.

The reaction of cephem compounds of the formula III with carboxylic acids of the formula IV or activated derivatives thereof can be carried out in a temperature range of about −80° to about +80° C., preferably between −30 and +50° C., but in particular between about −20° C. and room temperature.

The reaction time depends on the reactants, the temperature and the solvent or solvent mixture and is usually between about ¼ hour and about 72 hours.

If appropriate, the reaction with acid halides can be carried out in the presence of an acid-binding agent to bond the hydrogen halide liberated. Particularly suitable acid-binding agents are tertiary amines, such as, for example, triethylamine or dimethylaniline, inorganic basis, such as, for example, potassium carbonate or sodium carbonate, and alkylene oxides, such as, for example, propylene oxide.

The presence of a catalyst, such as, for example, dimethylaminopyridine, can in some cases also be advantageous.

If the amino group in the compounds of the general formula III is present in the form of a reactive derivative, this can be a derivative such as is known for amidation reactions from the literature. Thus, for example, possible derivatives are silyl derivatives which are formed in the reaction of compounds of the general formula III with a silyl compound, such as, for example, trimethylchlorosilane or bis-(trimethylsilyl)-acetamide. If the reaction is carried out with such a compound activated at the amino group, it is advantageous to use an inert solvent, such as, for example, methylene chloride, tetrahydrofuran or dimethylformamide.

The following embodiment examples for the compounds which can be prepared by the process according to the invention serve to further illustrate the invention, but do not limit it thereto.

EXAMPLE 1

7-[2-(2-Aminothiazol-4-yl)-2-syn-methoxyiminoacetamido]-3-[2,3-cyclopenteno-1-pyridinio)methyl]-ceph-3-em-4-carboxylate dihydriodide 2.72 g (10 mmol) of 7-aminocephalosporanic acid are suspended in 160 ml of dry methylene chloride, 7.1 ml (60 mmol) of 2,3-cyclopentenopyridine and then 7.1 ml (50 mmol) of trimethyliodosilane are added and the mixture is heated under reflux for 2 hours. The reddish brown-coloured solution is cooled to 0° and 4.77 g (15 mmol) of the activated ester of 2-(2-amino-1,3-thiazol-4-yl)-2-syn-methoxyiminoacetic acid with 1-hydroxybenzotriazole are added in portions in the course of 2 hours. The mixture is stirred at 20° C. for 17 hours and a solution of 25 g of potassium iodide in 200 ml of 2 N HCl is then added at 0°. After 3 hours at 0°, the precipitated is filtered off with suction, washed successively with methylene chloride, ice-water, acetone and ether and dried over $P_2O_5$ in vacuo. 5.35 g (68%) of the title compound are obtained in the form of light yellow crystals of decomposition point 179°–181° C.

$C_{22}H_{22}N_6O_5S_2$ ×2HI ×$H_2O$ (788.43): Calculated: C,33.51, H,3.32 I,32.19.;N,10.66;S,8.13; $H_2O$ 2.3%. Found: C, 33.6; H 3.6;I,31.3; N,10.7; S, 7.1; $H_2O$,2.5%.

IR (KBr): 1785 cm$^{-1}$ (lactam CO)

$^1$H-NMR (CF$_3$CO$_2$D): δ=2.30−2.85 (m, 2H, cyclopentene H); 3.10-4.05 (m, 6H, 4 cyclopentene H and SCH$_2$): 4.41 (s, 3H, OCH$_3$); 5.21-6.23 (m, 4H, CH$_2$Py and 2 lactam H); 8.11 (s, 1H, thiazole); and 7.65-8.70 ppm (m, 3H, Py).

EXAMPLE 2:

(a)

7-Amino-3-[(2,3-cyclopenteno-1-pyridinio)methyl]-ceph-3-em-4-carboxylate hydriodide Variant 1

First 35.7 g (35 ml, 0.3 mole) of 2,3-cyclopentenopyridine and then 36 ml (0.25 mole) of trimethyliodosilane are added successively to a suspension of 13.6 g (0.05 mole) of 7-aminocephalosporanic acid in 500 ml of dry methylene chloride. The mixture is heated under reflux for 2 hours and cooled, and a mixture of 350 ml of ethanol and 50 ml of water is added dropwise, while stirring. During the dropwise addition, a precipitate forms, and, after the mixture has been left to stand overnight in a refrigerator, this is filtered off with suction, and washed successively with two 80 ml portions of isopropanol, 80 ml of acetone and with 100 ml of ether. After drying over $P_2O_5$ in vacuo, 19.5 g (82% of theory) of a brownish finely crystalline product of decomposition point 160°–165° C. are obtained.

$C_{16}H_{17}N_3O_3S$×HI×$H_2O$ (477.3): Calculated: C, 40.26;H,4.22; I,26.59;N,8.80; S,6.72%. Found: C,38.7; H,4.2; I,26.6; N,8.5; S,6.4% .

IR (KBr): 1785 cm$^{-1}$ (lactam CO)

$^1$H-NMR (CF$_3$CO$_2$D): δ 2.3–2.8 (m, 2H, cyclopentene H); 3.1–3.9 (m, 6H, 4 cyclopentene H and SCH$_2$); 5.3–6.3 (m, 4H, CH$_2$Py and 2 lactam H); and 7.6–8.8 ppm (m, 3H, Py).

Variant 2

63.5 g (0.5 mole) of iodine are added in portions to 43.8 g (0.30 mole) of hexamethyldisilane at 70°-75° C. and, after the addition, the solution is heated under reflux for 1 hour. It is cooled and diluted with 1 l of methylene chloride, 71 ml (0.6 mole) of 2,3-cyclopentenopyridine are added and then 27.2 g (0.1 mole) of 7-amino-cephalosporanic acid are added all at once. The mixture is heated under reflux for 2 hours and then cooled to 0°-5° and worked up as described above (variant 1). 39.6 g (83% of theory) of light brown crystals are obtained. The compound is identical in all its properties to that described above.

(b)
7-[2-(2-Aminothiazol-4-yl)-2-syn-methoxyiminoacetamido]-3-[2,3-cyclopenteno-1-pyridinio)methyl]-ceph-3-em-4carboxylate dihydriodide A solution of an activated ester is prepared from 2 g (10 mmol) of 2-(2-amino-1,3-thiazol-4-yl)-2-synmethoxyiminoacetic acid, 1.7 g (11 mmol) of 1-hydroxybenzotriazole hydrate and 2.3 g (11 mmol) of dicyclohexylcarbodiimide in 30 ml of N,N-dimethylformamide. After the mixture has been stirred at room temperature for 3 hours, the dicyclohexylurea is filtered off and the solution is added dropwise to a solution of 2.4 g (5 mmol) of the hydriodide of stage a and 0.4 ml (5 mmol) of pyridine in 5 ml of water and 40 ml of N,N-dimethylformamide at 0°-5°. After 17 hours at room temperature, the solvent is removed in vacuo and the residue is digested with 20 ml of water. A small amount of insoluble material is filtered off, a solution of 3.3 g (20 mmol) of potassium iodide in 10 ml of 2 N HCl is added to the filtrate and, after the mixture has been left to stand overnight in a refrigerator, the precipitate formed is filtered off with suction. It is washed with a little ice-water and dried over $P_2O_5$. Yield: 1.9 g (48% of theory) of light yellow crystals. The compound is identical in all its properties to that from Example 1.

EXAMPLE 3

7-[2-(2-Aminothiazol-4-yl)-2-syn-methoxyiminoacetamido]-3-[2,3-cyclopenteno-1-pyridinio)methyl]-ceph-3-em-4-carboxylate monohydriodide 1.1 g (5.5 mmol) of 2-(2-amino-1,3-thiazol-4-yl)-2-synmethoxyiminoacetic acid, 0.9 g (5.9 mmol) of 1-hydroxybenzotriazole hydrate and 1.2 g (5.8 mmol) of dicyclohexylcarbodiimide in 50 ml of N,N-dimethylformamide are stirred at room temperature for 4 hours. The dicyclohexylurea is filtered off and the solution of the activated ester is cooled to 0° C. 2.33 g (4.9 mmol) of 7-amino-3-[(2,3-cyclopenteno-1-pyridinio) methyl]-ceph-3-em-4-carboxylate hydriodide (Example 2a) and 2.5 ml of water are then added and the mixture is stirred at room temperature for 17 hours. A small amount of insoluble material is filtered off and the filtrate is freed from the solvent on a rotary vacuum evaporator. The oily residue is mixed with 30 ml of ethanol and the precipitate formed is filtered off with suction, washed several times with ethanol and dried in vacuo.

Yield: 2.7 g (86% of theory)

$C_{22}H_{22}N_6O_5S_2 \times HI$ Calculated: C,41.13;H,3.61;N,13.08;S, 9.98;I,19.75%. Found: C,40.6;C,3.9;N,12.5;S,10.5T,16.8%.

$^1$H-NMR (CF$_3$CO$_2$D): δ=2.3-2.85 (m, 2H, cyclopentene H); 3.15-3.95 (m, 6H, 4 cyclopentene H and SCH$_2$); 4.42 (s, 3H, OCH$_3$); 5.2-6.2 (m, 4H, CH$_2$Py and 2 lactam H); 8.13 (s, 1H, thiazole); and 7.65-9.0 ppm (m, 3H, Py).

EXAMPLE 4

7-[2-(5-Amino-1,2,4-thiadiazol-3-yl)-2-syn-methoxyiminoacetamido]-3-[(2,3-cyclopenteno-1-pyridinio)-methyl]-ceph-3-em-4-carboxylate 0.2 g (1 mmole) of 2-(5-amino-1, 2,4-thiadiazol-3-yl)-2-syn-methoxyiminoacetic acid, 140 mg (1.04 mmol) of 1-hydroxybenzotriazole hydrate and 206 mg (1 mmol) of dicyclohexylcarbodiimide in 3 ml of N,N-dimethylformamide are stirred at room temperature for 2.5 hours. The reaction solution is filtered and the dicyclohexylurea is washed with 0.5 ml of dimethylformamide. A solution of 365 mg (1.1 mmol) of 7-amino-3-[(2,3-cyclopenteno-1-pyridinio)methyl]-ceph-3-em-4-carboxylate in 4 ml of N,N-dimethylformamide and 0.4 ml of water is added to the filtrate and the mixture is stirred at room temperature for 3 hours. The solvent is removed on a rotary vacuum evaporator and the residue is dissolved in 5 ml of water and chromatographed over a Lobar B silica gel column (Merck, Darmstadt, Cat. No. 10401) using acetone:water (2:1). The product fractions are concentrated and freeze-dried.

Yield: 284 mg (55% of theory) of colourless amorphous product

IR (KBr): 1770 cm$^{-1}$ (lactam CO)

$^1$H-NMR (CF$_3$CO$_2$D): δ=2.25-2.85 (m, 2H, cyclopentene H); 3.1-4.05 (m, 6H, 4 cyclopentene H and SCH$_2$), 4.30 (s, 3H, OCH$_3$); 5.2-6.2 (m, 4H, CH$_2$Py and 2 lactam H); 7.66-8.0 (m, 1 Py-H); and 8.16-8.7 ppm (m, 2H, Py).

The following compounds of the general formula III'

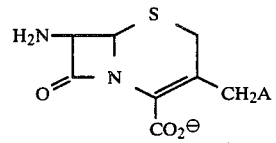

are obtained analogously to Example 2a from 7-aminocephalosporanic acid and the corresponding bases on which the radical A is based.

TABLE 1

Compounds

| Example$^{(x)}$ | A | Yield % of theory | $^1$H—NMR in CF$_3$CO$_2$D: δ (ppm) |
|---|---|---|---|
| 1 | ⊕—N⟨⟩ | 36 | 3.3-3.75 (AB, 2H, SCH$_2$); 5.3-6.6 (m, 4H, CH$_2$Py and 2 lactam H); and 7.9-9.45 (m, 5H, Py). |

TABLE 1-continued

Compounds

[Structure: β-lactam with H₂N-, S, N, CO₂⁻, CH₂A]

| Example(x) | A | Yield % of theory | ¹H—NMR in CF₃CO₂D: δ (ppm) |
|---|---|---|---|
| II | [quinolinium, −N⊕] | 16 | 3.4–3.9 (AB, 2H, SCH₂); 5.2–6.4 (m, 4H, CH₂Py and 2 lactam H); 7.9–8.8 (m, 5 quinoline H); and 8.85–9.2 (m, 2 quinoline H). |
| III | [isoquinolinium, −N⊕] | 35 | 3.5–4.0 (AB, 2H, SCH₂); 5.1–6.6 (m, 4H, CH₂Py and 2 lactam H); 7.9–8.8 (m, 6 isoquinoline H); and 9.8–9.95 (bs, 1 isoquinoline H). |
| IV | [5,6,7,8-tetrahydroquinolinium, −N⊕, H] | 38 | 1.7–2.4 (m, 4H, cyclohexene H); 2.7–3.95 (m, 6H, 4 cyclohexene H and SCH₂); 5.35–6.25 (m, 4H, CH₂Py and 2 lactam H); and 7.75–8.65 (m, 3H, Py). |
| V | [methylquinolinium, −N⊕—CH₃ X⁻] HI | 53 | 3.15 (s, 3H, CH₃); 3.2–4.0 (AB, 2H, SCH₂); 5.1–6.8 (m, 4H, CH₂Py and 2 lactam H); and 7.8–9.3 (m, 6H, quinoline). |
| VI | [methylpyridinium, CH₃ on ring, −N⊕ × HI] | 67 | 2.69 (s, 3H, CH₃); 3.66 (s, 2H, SCH₂); 5.25–6.39 (m, 4H, CH₂Py and 2 lactam H); and 7.83–9.03 (m, 4Py—H). |

(x)The compounds of Example I–IV are obtained in amorphous form from the crude hydriodide salts by chromatography over silica gel, and the compounds of Examples V and VI are isolated directly as hydriodide salts.

EXAMPLE 5

7-[2-(2-Aminothiazol-4-yl)-2-syn-methoxyiminoacetamido]-3-[(2,3-cyclopenteno-1-pyridinio)-methyl]-ceph-3-em-4-carboxylate 1.05 g (3 mmol) of S-2-benzothiazolyl 2-(2-amino-1,3-thiazol-4-yl)-2-syn-methoxyiminothioacetate are added to a solution, cooled to 5°, of 1.02 g (2.5 m-moles) of 7-amino-3-[(2,3-cyclopenteno-1-pyridinio)methyl]-ceph-3-em-4-carboxylate dihydrochloride in 12.5 ml of N,N-dimethylformamide and 1.25 ml of water, and the mixture is stirred at 5°–10° C. for 3 hours. The solvent is removed in vacuo, the residue is dissolved in 5 ml of water and the solution is brought to pH 6 with sodium bicarbonate and chromatographed over silica gel (Lobar C column, Merck, Cat. No. 10402), using acetone:water (2:1). The product fractions are freeze-dried to give 0.86 g (66% of theory) of light yellow product.

¹H-NMR (CF₃CO₂D): δ=2.40–2.75 (m, 2H, cyclopentene H); 3.22–4.23 (m, 6H, 4 cyclopentene H and SCH₂); 4.26 (s, 3H, OCH₃); 5.25–6.36 (m, 4H, CH₂Py and 2 lactam H); 7.38 (s, 1H, thiazole); and 7.66–8.58 ppm (m, 3H, Py).

The following compounds of the general formula I′ are obtained analogously to Example 5 from the compounds of Examples I–VI (Table 1) and the 2-mercaptobenzothiazoleactivated ester of 2-(2-amino-1,3-thiazol-4-yl)-2-synmethoxyiminoacetate.

TABLE 2

Compounds I′

[Structure: aminothiazolyl-methoxyimino-cephalosporin with CH₂A substituent]

| Example | A (Example No. of the starting compound) | Yield % of theory | ¹H—NMR in CF₃CO₂D: δ (ppm) |
|---|---|---|---|
| 6 | (I) [pyridinium, −N⊕] | 71 | 3.52 and 3.96 (AB, J = 19Hz, 2H, SCH₂); 4.26 (s, 3H, OCH₃); 5.2–6.45 (m, 4H, CH₂Py and 2 lactam H); 7.43 (s, thiazole H); and 7.9–9.2 (m, 5H, Py) |
| 7 | (II) [quinolinium] | 62 | 3.40 and 3.80 (AB, J = 19Hz, 2H, SCH₂); 4.21 (s, 3H, OCH₃); 5.30–6.50 (m, 4H, 3-CH₂ and 2 lactam H with 1 d each at 5.41 and 6.10, J = 5Hz, C₆ and C₇—H); 7.42 (s, 1H, thiazole; 7.95–8.65 (m, 5H, quinoline H); and 8.95–9.40 ppm (m, 2H, quinoline H) |
| 8 | (III) [isoquinolinium] | 58 | 3.45 and 3.93 (AB, J = 18Hz, 2H, SCH₂); 4.21 (s, 3H, OCH₃); 5.25–6.50 (m, 4H, 3-CH₂ and lactam H); and 7.41 (s, 1H, thiazole); 7.95–8.80 (m, 6H, isoquinoline H); and 9.79 ppm (bs, 1H, isoquinoline H) |
| 9 | (IV) [tetrahydroquinolinium, H] | 66 | 1.7–2.4 (m, 4H, cyclohexene H); 2.7–3.5 (m, 4H, cyclohexene H); 3.50 and 3.70 (AB, J = 19Hz, 2H, SCH₂); 4.25 (s, 3H, OCH₃); 5.38 (d, J = 5Hz, C₆—H); 5.55 and 5.80 (AB, 2H, CH₂Py); 6.08 (d, J = 5Hz, C₇—H); 7.39 (s, 1H, thiazole); and 7.65–8.58 (m, 3H, Py) |

TABLE 2-continued

Compounds

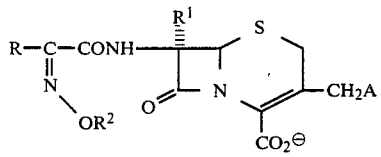

| Example | A (Example No. of the starting compound) | Yield % of theory | $^1$H—NMR in CF$_3$CO$_2$D: δ (ppm) |
|---|---|---|---|
| 10 | (V) 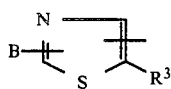 | 61 | 3.15 (s, 3H, CH$_3$); 3.3 and 3.7 (AB, 2H, SCH$_2$); 4.25 (s, 3H, OCH$_3$); 5.1–6.7 (m, 4H, CH$_2$Py and 2 lactam H); 7.4 (s, 1H, thiazole); and 7.8–9.2 (m, 6H, lepidine) |
| 11 | (VI) 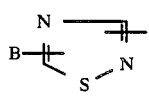 | 72 | 2.60 (s, 3H, PyCH$_3$); 3.63 and 3.86 (AB, J = 19Hz, 2H, SCH$_2$); 4.24 (s, 3H, OCH$_3$); 5.15–6.55 (m, 4H, CH$_2$Py and 2 lactam H); 7.42 (s, 1H, thiazole); and 7.75–9.05 (m, 4H, Py). |

We claim:

1. A process for the preparation of a cephem compound of the formula I

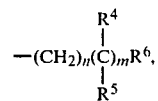

in which R denotes a thiazolyl radical

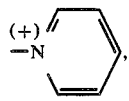

or a 1,2,4-thiadiazolyl radical

[structure]

in which
R$^3$ represents hydrogen or halogen and B represents an amino group or an amino group substituted with an amino protective group, and wherein
R$^1$ denotes hydrogen,
R$^2$ denotes hydrogen, C$_1$–C$_6$-alkyl, which can be monosubstituted or polysubstituted by halogen, C$_1$–C$_6$-alkylthio, C$_1$–C$_6$-alkoxy, phenyl or 1,3-thiazol-4-yl or denotes C$_2$–C$_6$-alkenyl, which can be monosubstituted or polysubstituted by halogen; or denotes C$_2$–C$_3$-alkinyl, C$_3$–C$_6$-cycloalkyl, C$_3$–C$_6$-cycloalkyl-C$_1$–C$_6$-alkyl, C$_4$–C$_7$-cycloalkeyl, or the group $-(CH_2)_n(C)_mR^6$,
with R$^4$ above and R$^5$ below the C in which m and n are each 0 or 1,
R$^4$ and R$^5$ can be identical or different and denote hydrogen, phenyl or a C$_1$–C$_4$-alkyl group, or, together with the carbon to which they are bonded, form a vinylidene or C$_3$–C$_7$-cycloalkylidene group,
R$^6$ denotes a COOH, CN or CONH$_2$ group, it being possible for the latter to be monosubstituted or disubstituted on the nitrogen by methyl or ethyl,
A denotes a quinolinium or isoquinolinium radical, each of which can also be monosubstituted or polysubstituted by identical or different substituents from the group comprising
C$_1$–C$_6$-alkyl, which can be substituted by hydroxyl; halogen,
trifluoromethyl and
hydroxyl, or denotes a pyridinium radical

[structure: (+)—N pyridinium]

which can be monosubstituted or polysubstituted by identical or different substituents from the group comprising
C$_1$–C$_6$-alkyl, which can be monosubstituted or polysubstituted by hydroxyl; formyl and C$_1$–C$_6$-alkylcarbonyl, sulfo, carbamoyl, C$_1$–C$_6$-alkoxy and hydroxy-C$_1$–C$_6$-alkoxy, it also being possible for 2 neighbouring alkyl groups to be linked to form a tri- to pentamethlene ring in which one ring carbon atom can be replaced by an oxygen or sulfur atom and which can furthermore also contain one or two double bonds, and which may be substituted by C$_1$–C$_6$-alkyl, C$_1$–C$_4$-alkoxy, hydroxymethyl, halogen, hydroxyl, oxo or exomethylene,
C$_2$–C$_6$-alkenyl, which can be substituted by hydroxyl,
C$_2$–C$_6$-alkinyl,
C$_3$–C$_7$-cycloalkyl and C$_3$–C$_7$-cycloalkylmethyl, it being possible for the ring in these two substituents also to be substituted by hydroxyl or halogen,
C$_4$–C$_7$-cycloalkenyl,
C$_1$–C$_6$-alkoxy, which can be substituted by hydroxyl, C$_2$–C$_6$-alkenyloxy and C$_2$–C$_6$-alkinyloxy,
halogen, trifluoromethyl and hydroxyl; phenyl, benzyl which can also be substituted by halogen, 2'-thienyl or 3'-thienyl, formyl, C$_1$–C$_6$-alkylcarbonyl, which can also be substituted by hydroxyl,
phenylcarbonyl and
carbamoyl,
and in which the R$^2$O group is in the syn-position, which comprises reacting a compound of the formula II

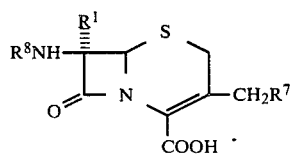

in which $R^1$ has the meaning given for formula I, $R^7$ denotes a group which can be replaced by the base which corresponds to the radicals A of formula I and $R^8$ represents hydrogen or an amino-protective group, with a molar excess of the base on which the radical A defined in formula I is base and in the presence of tri-$C_1$–$C_4$-alkyl-iodosilane to form the compound of the formula III

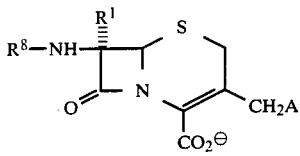

in which $R^1$, $R^8$ and A have the above-mentioned meaning, and said base is also present in molar excess related to said tri-$C_1$–$C_4$-alkyl-iodosilane and (a) splitting off any amino-protective group which may be present and (b) reacting the compound III, in which $R^8$ dentoes hydrogen, either as such or in the form of a reactive derivative, with a 2-syn-oxyiminoacetic acid of the formula IV

in which R and $R^2$ have the meaning given, or with its activated derivative.

2. The process as claimed in claim 1, wherein the tri-$C_1$–$C_4$-alkyliodosilane is trimethyl- or triethyl-iodosilane.

* * * * *